(12) United States Patent
Injev (10) Patent No.: US 8,608,681 B2
(45) Date of Patent: Dec. 17, 2013

(54) INFUSION PRESSURE MONITORING SYSTEM

(75) Inventor: Valentine P. Injev, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/607,069

(22) Filed: Sep. 7, 2012

(65) Prior Publication Data

US 2012/0330337 A1 Dec. 27, 2012

Related U.S. Application Data

(62) Division of application No. 12/786,494, filed on May 25, 2010, now Pat. No. 8,287,486.

(51) Int. Cl.
*A61B 17/20* (2006.01)
(52) U.S. Cl.
USPC .......................................................... 604/22

(58) Field of Classification Search
USPC ............................................................ 604/22
See application file for complete search history.

(56) References Cited

U.S. PATENT DOCUMENTS 7,981,073 B2 * 7/2011 Mollstam et al. ............... 604/28

* cited by examiner

*Primary Examiner* — Jason Flick
(74) *Attorney, Agent, or Firm* — Kenneth D. Bassinger (57) ABSTRACT

An infusion pressure monitoring system for a phacoemulsification or vitrectomy machine to be operated by a health care provider includes an irrigation path configured to carry an irrigation solution to a surgical site and a fluid sensor configured to detect a fluid parameter in the irrigation path. An input device receives a variable fluid flow command from the health care provider commanding an irrigation fluid flow through the irrigation path at a flow rate corresponding to the command. A controller communicates with both the fluid sensor and the input device. The controller determines an expected fluid pressure value and a dynamically variable threshold pressure value based upon the variable fluid flow command.

16 Claims, 3 Drawing Sheets

INFUSION PRESSURE MONITORING SYSTEM

This Application is a division of U.S. application Ser. No. 12/786,494 filed May 25, 2010.

BACKGROUND OF THE INVENTION

The present invention relates to an infusion pressure monitoring system for a phacoemulsification or vitrectomy system.

A typical surgical instrument suitable for phacoemulsification procedures on cataractous lenses includes an ultrasonically driven phacoemulsification hand piece, an attached hollow cutting needle surrounded by an irrigating sleeve, and an electronic control console. The hand piece is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece.

During a phacoemulsification procedure, the tip of the cutting needle and the end of the irrigation sleeve are inserted into the anterior segment of the eye through a small incision in the eye's outer tissue. The surgeon brings the tip of the cutting needle into contact with the lens of the eye, so that the vibrating tip fragments the lens. The resulting fragments are aspirated out of the eye through the interior bore of the cutting needle, along with irrigation fluid provided to the eye during the procedure, and into a waste reservoir.

Throughout the procedure, irrigating fluid is infused into the eye, passing between the irrigation sleeve and the cutting needle and exiting into the eye at the tip of the irrigation sleeve and/or from one or more ports or openings formed into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

Conventional systems employ fluid-filled bottles or bags hung from an intravenous (IV) pole as an irrigation fluid source. Irrigation flow rates, and corresponding fluid pressure at the eye, are regulated by controlling the height of the IV pole above the surgical site. For example, raising the IV pole results in a corresponding increase in head pressure and thus increase in fluid pressure at the eye, resulting in a corresponding increase in irrigation flow rate. Likewise, lowering the IV pole results in a corresponding decrease in pressure at the eye and corresponding irrigation flow rate to the eye.

Aspiration flow rates of fluid from the eye are typically regulated by an aspiration pump. The pump action produces aspiration flow through the interior bore of the cutting needle. The aspiration flow results in the creation of vacuum at the aspiration line. The aspiration flow and/or vacuum are set to achieve the desired working effect for the lens removal. The IV pole height and infusion pump are regulated to achieve a proper intra-ocular chamber balance in an effort to maintain a relatively consistent fluid pressure at the surgical site within the eye.

While a consistent fluid pressure in the eye is desirable during the phacoemulsification procedure, common occurrences or complications create fluctuations or abrupt changes in fluid flow and pressure at the eye. These fluctuations or changes occur for a number of reasons. For example, depleting the fluid reservoir, inadvertently separating the irrigation line and hand piece, leaking fluid from the line or from a connector between lines, and kinking the irrigation line can all result in pressure fluctuations or abrupt pressure changes leading to surgical complications.

Some of today's systems are equipped with irrigation/infusion pressure sensors, which have the ability to monitor the infusion pressure and forewarn the user of pressure drops. These systems monitor relative to a fixed reference point. For example, the system may detect when the pressure falls below a set, single pressure value for all points during a surgical procedure. Since this set, single pressure value is of necessity somewhere below the lowest expected pressure for a surgical procedure, in some instances, a complication arising when the pressure is high may not be detected until after substantial drop in pressure, resulting in a relatively slow reaction time. A slow reaction time may result in, among other undesirable complications, shallowing or collapse of the anterior eye chamber and possible thermal event to the cornea (if ultrasound is in use) at the incision site due to the reduced or eliminated irrigation flow.

Therefore, there remains a need for an improved system response to unexpected pressure drops that can occur during a medical procedure. The present disclosure is directed to addressing one or more of the deficiencies in the prior art.

SUMMARY OF THE INVENTION

In one exemplary aspect consistent with the principles herein, the present disclosure is directed to an infusion pressure monitoring system for a phacoemulsification or vitrectomy machine to be operated by a health care provider. The system includes an irrigation path configured to carry an irrigation solution to a surgical site and a fluid sensor configured to detect a fluid parameter in the irrigation path. An input device is configured to receive a variable infusion pressure or infusion fluid flow command from the health care provider. This variable fluid pressure or flow command instructs the system to provide an irrigation fluid flow through the irrigation path at the pressure or flow rate corresponding to the command. A controller communicates with both the fluid sensor and the input device. The controller is configured to determine an expected fluid pressure value and to determine a dynamically variable threshold pressure value based upon the variable fluid flow command.

In one aspect, the controller is configured to compare the detected fluid parameter (from the sensor) to the determined dynamically variable threshold pressure value. When the detected fluid parameter is less than the determined dynamically variable threshold pressure value, the controller triggers a fault condition.

In another exemplary aspect, the present disclosure is directed to an infusion pressure monitoring system for a phacoemulsification or vitrectomy machine to be operated by a health care provider. The system includes a hand piece configured to perform a surgical procedure on a patient. An irrigation path is associated with the hand piece and configured to carry an irrigation solution to a surgical site. A fluid sensor is configured to detect a fluid pressure in the irrigation path. The system includes a foot pedal configured to receive a variable fluid command from the health care provider commanding an irrigation fluid characteristic through the irrigation path at a pressure or flow rate corresponding to the command. A controller is in communication with the fluid sensor and in communication with the input device. The controller is configured to determine an expected fluid pressure value based upon the variable fluid command and configured to determine a dynamically variable threshold pressure value based upon the expected fluid pressure value.

In another exemplary aspect, the present disclosure is directed to a method of operating a phacoemulsification machine. The method includes the steps of receiving measured pressure data at a controller indicative of a measured infusion pressure and receiving from an input device a variable fluid pressure or flow command. The method includes determining a variable expected fluid pressure value corresponding to the variable pressure or flow command and determining whether the measured infusion pressure data is within an acceptable pressure range for the expected fluid pressure value. The acceptable pressure range is defined by a dynamically variable threshold value. A fault condition is triggered when the measured infusion pressure data is not within the acceptable pressure range and an operating parameter of the phacoemulsification machine is changed in response to the fault condition. In one aspect, the method also includes determining the dynamically variable threshold value based on the variable expected fluid pressure value.

It is to be understood that both the foregoing general description and the following detailed description are exemplary and explanatory only and are intended to provide further explanation of the invention as claimed. The following description, as well as the practice of the invention, sets forth and suggests additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

The system and methods described herein monitor positive infusion pressure, or in the case of cataract surgery, positive intra-ocular pressure (IOP) during anterior segment surgery, in order to provide a dynamically variable minimum threshold pressure.

Using a measured infusion pressure value obtained by an irrigation line pressure sensor and using a commanded operating flow based upon a real-time user flow command at an input device, the system determines a dynamically variable minimum acceptable pressure threshold. To do this, the system takes into account one or more system operating parameters that affect the infusion pressure, such as the commanded aspiration pump flow, the commanded irrigation flow, vacuum level, and bottle height. It may also take into account known equipment variables such as hand piece tip type, infusion sleeve size, and other variables that affect the infusion pressure. Taking into account these known operating parameters and equipment variables, the system predicts the expected infusion pressure drop under normal operating conditions for various commanded aspiration flow rates. Due to its dynamic monitoring, the system can provide a relatively precise or tight dynamically variable minimum threshold for the current commanded aspiration flow rate. If the system detects an actual pressure below the dynamically variable minimum threshold, the system alerts the health care provider to take corrective action.

Thus, when a large aspiration flow is produced, the system recognizes the expected infusion pressure drop and monitors the event on a continuous basis, in a relatively precise manner with the dynamically variable minimum pressure threshold, instead of a single static pressure value for all flow commands, as done in the prior art.

Figure 1:
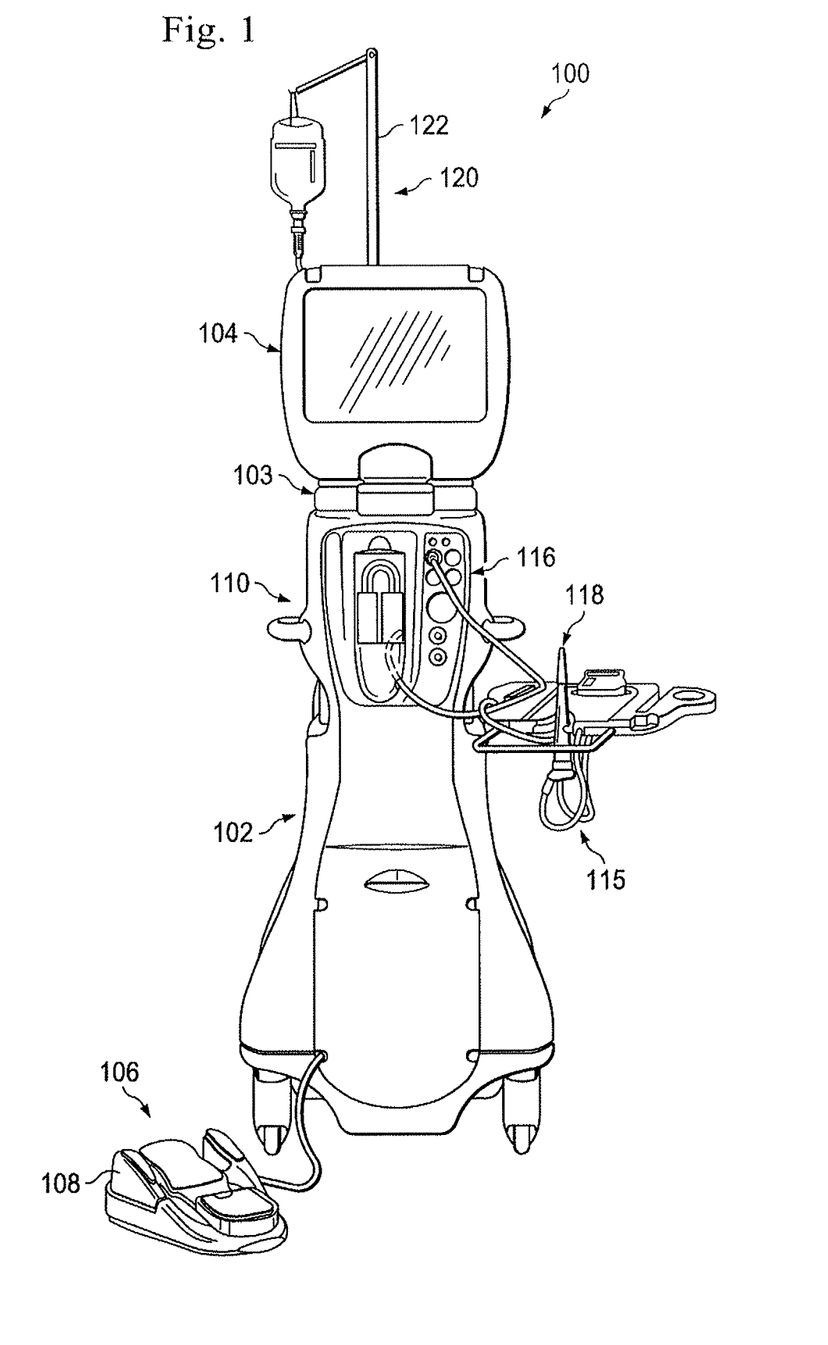
FIG. 1 is an illustration of an exemplary emulsification surgical machine having a configurable machine interface using the principles and methods described herein.

FIG. 1 illustrates an emulsification surgical machine, generally designated 100, according to an exemplary embodiment. The machine 100 includes a base housing 102 with a computer unit 103 and an associated display screen 104 showing data relating to system operation and performance during an emulsification surgical procedure. The machine 100 also includes a number of subsystems that are used together to perform the emulsification surgical procedures. For example, the subsystems include a footpedal subsystem 106 including, for example, a footpedal 108, a fluidics subsystem 110 including an aspiration vacuum and an irrigation pump that connect to tubing 115, an ultrasonic generator subsystem 116 including an ultrasonic oscillation hand piece 118, and an IV pole subsystem 120 including a motorized IV pole 122. Some embodiments also include a vitrectomy cutter subsystem including a vitrectomy hand piece. To optimize performance of the different subsystems during surgery, their operating parameters differ according to, for example, the particular procedure being performed, the different stages of the procedure, the surgeon's personal preferences, whether the procedure is being performed in the anterior or posterior portion of the patient's eye, and so on.

The different subsystems in the base housing 102 comprise control circuits for the operation and control of the respective microsurgical hand pieces. The controller 103 governs the interaction and relationship between the different subsystems to properly perform an emulsification surgical procedure. To do this, it includes a processor and memory and is configured or programmed to control the machine, based upon pre-established programs or sequences.

As shown in FIG. 1, the display screen 104 rests on the base housing 102 for viewing and access by the operator. An input device permits a user to control images on the display and to make selections within a limited scope to control or modify the preprogrammed relationships between different subsystems. In this embodiment, the input device is a touch screen device responsive to selections made directly on the screen.

Figure 2:
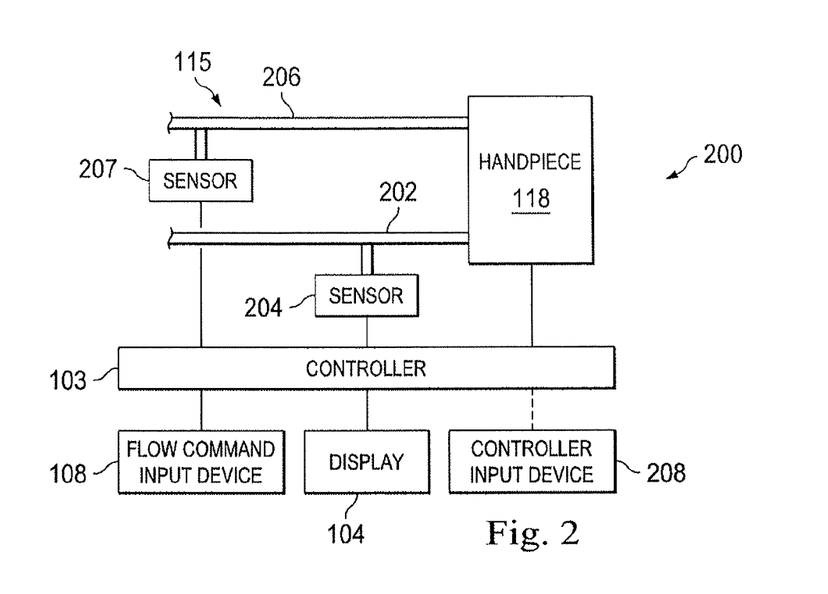
FIG. 2 is a block diagram of an exemplary infusion pressure monitoring system of the exemplary emulsification surgical machine of FIG. 1.

FIG. 2 is a block diagram representing particular components of the machine 100 in FIG. 1. Here the schematic includes certain components of the subsystems identified above. Together, these components comprise an infusion pressure monitoring system 200 that includes an irrigation path 202, an irrigation pressure sensor 204 in or associated with the irrigation path 202, an aspiration path 206, an aspiration pressure sensor 207 in or associated with the aspiration path 206, the hand piece 118, a flow command input device identified as the foot pedal 108, the display 104 and an associated controller input device 208 for entering data or commands for programming the system.

The irrigation path 202 extends between a sterile solution reservoir (not shown in FIG. 2) and the hand piece 118 and carries sterile fluid from the reservoir to the hand piece for irrigating an eye during a surgical procedure. In one example, the sterile fluid is a saline fluid, however, other fluids may be used. At least a portion of the irrigation path 202 may be formed of a flexible tubing, and in some embodiments, the path 202 is formed of multiple segments, with some segments being rigid and others being flexible.

The irrigation sensor 204 is associated with the irrigation path 202 and performs the function of measuring the infusion pressure in the irrigation path 202. In some embodiments, the sensor 204 is a pressure sensor configured to detect current pressure conditions. The sensor 204 communicates signals indicative of the sensed pressure to the controller 103. Once received, the controller 103 processes the received signals to determine whether the measured pressure is above or below the dynamically variable pressure threshold value, or within a pre-established desired pressure range. Although described as a pressure sensor, the irrigation sensor 204 may be another type of sensor, such as a flow sensor that detects actual fluid flow and may include additional sensors for monitoring additional parameters. In some embodiments, the sensor 204 includes its own processing function and the processed data is then communicated to the controller 103.

The aspiration path 206 extends from the hand piece to the drain reservoir 304. The aspiration path 206 carries away fluid used to flush the eye as well as any emulsified particles.

The aspiration sensor 207 is associated with the aspiration path 206 and performs the function of measuring the waste fluid pressure in the aspiration path 206. Like the sensor 204 described above, the sensor 207 may be a pressure sensor configured to detect current pressure conditions. It communicates signals indicative of the sensed pressure to the controller 103. The sensor 207, like the sensor 204 may be any suitable type of sensor, such as a flow sensor that detects actual fluid flow and may include additional sensors for monitoring additional parameters.

The hand piece 118 is identified as an ultrasonic hand piece that carries the irrigation fluid to the surgical site. The hand piece is configured as known in the art to receive and operate with different needles or equipment depending on the application and procedure being performed. It should be noted that although an ultrasonic hand piece is discussed, the principles of the invention are intended to cover the use of vitrectomy cutter hand pieces or other hand pieces known in the art. For ease of reference only, the remainder of the application will refer only to the ultrasonic hand piece 118, recognizing that the system operates in a similar manner with other hand pieces.

In the example shown, the fluid command input device 108 is the foot pedal in FIG. 1. It can receive inputs indicative of a desired flow rate, desired pressure, or other fluid characteristic. It is configured to control the operational setting of the machine 100 through a plurality of major control settings, including controlling the irrigation flow rate or pressure within each of the major control settings. In some embodiments, the flow command input device is not a foot pedal, but is another input device, located elsewhere on the machine 100.

The controller input device 208 permits a user to enter data or commands that affect system programming. In this embodiment, the controller input device 208 is associated with the display 104. However, it could be associated directly with the controller in a manner known in the art. For example, in some embodiments, the controller input device 208 is a standard computer keyboard, a standard pointing device, such as a mouse or trackball, or other input device are also contemplated.

As described further below, some embodiments permit a user to enter desired ranges or percentages that define the location of the dynamically variable minimum pressure threshold relative to the expected pressure for a particular flow command generated by the input device foot pedal.

As is apparent from FIG. 2, the controller 103 communicates with the display 104, the flow command input device 108, the hand piece 118, the sensor 204, and the controller input device 208. It is configured or programmed to control the infusion pressure monitoring system 200 based upon pre-established programs or sequences.

In use, the controller 103 is configured to receive signals from the irrigation sensor 204 and process the signals to determine whether the detected infusion pressure is outside of dynamically variable acceptable ranges or above or below dynamically variable acceptable thresholds. If the controller 103 detects an unacceptable infusion pressure, it generates a fault signal and begins a mitigation sequence to protect the patient and the equipment.

Figure 3:
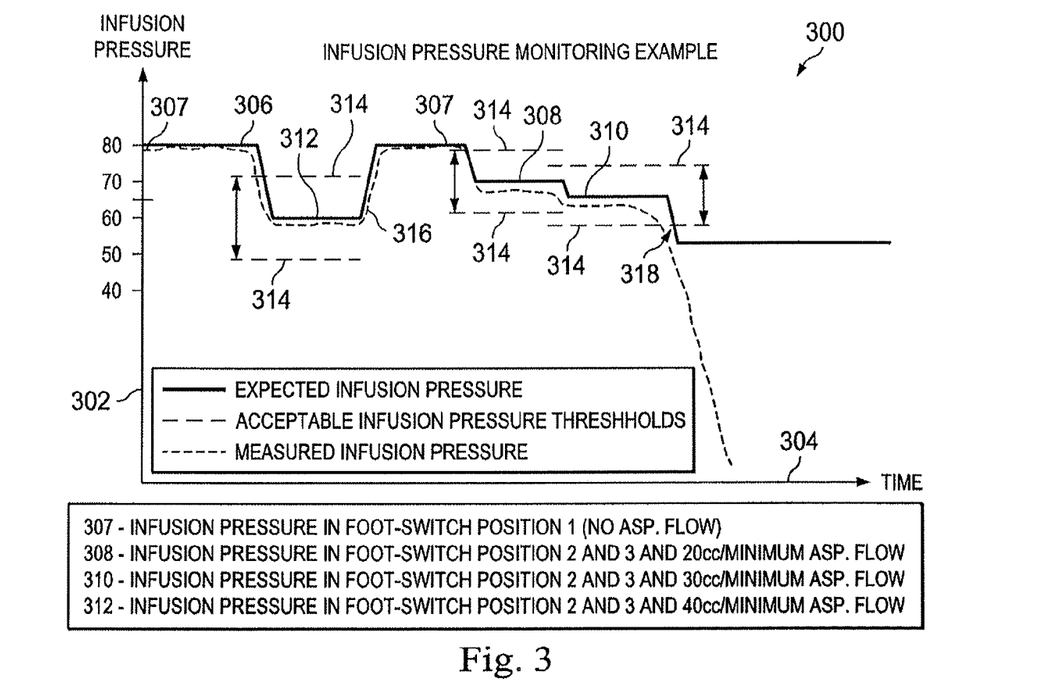
FIG. 3 is a graph representing an expected infusion pressure for a particular flow command, a dynamically variable infusion pressure threshold for the expected infusion pressure, and an actual measured pressure value.

FIG. 3 is a graph 300 showing an example of infusion pressure monitoring performed by the system 200 described herein. In this example, the vertical axis 302 of the graph 300 represents infusion pressure and the horizontal axis 304 represents time. The example includes an expected infusion pressure for each flow command input from the foot pedal 108, as the flow command input device. In FIG. 3, the expected infusion pressure corresponding to each flow command input is identified by the solid line, labeled 306. When the foot pedal is not depressed, the aspiration flow command is set to zero. Accordingly, the expected static infusion pressure can be readily determined based on the height of the IV pole carrying the fluid source. Embodiments using pumps or other pressure driving apparatus are as equally predictable at the static condition.

When the foot pedal 108 is depressed by a health care provider, the controller 103 generates a flow command and the machine 100 provides irrigation fluid flow through the irrigation line at the commanded flow rate. The commanded flow rate corresponds to the displacement of the food pedal. Depending on the input (or the displacement amount of the foot pedal), the flow can vary, for example, between a flow rate of just over 0 cc/min to 100 cc/min, for example. The flow rate, whether large or small, is controlled by the foot pedal depression amount.

FIG. 3 includes two examples where the foot pedal is not depressed by the health care provider. Accordingly, in this example, the expected pressure is static at 80 H2O as identified at 307.

FIG. 3 also includes three examples where the foot pedal is depressed by the health care provider, but with varied displacement resulting is varied commanded flow rates. For example, referring to the graph 300, at 308 the expected infusion pressure of 70 cm H2O is based on a commanded flow rate of, for example, 20 cc/min, at 310 the expected infusion pressure of 65 cm H2O is based on a commanded flow rate of 30 cc/min, and at 312 the expected infusion pressure of 60 cm H2O is based on a commanded flow rate of 40 cc/min. These are exemplary relationships used only for describing the system herein.

As shown in FIG. 3, the expected infusion pressure for a higher flow is less than the expected infusion pressure for a lower flow. Accordingly, the expected infusion pressure 310 corresponding to a commanded flow rate of 30 cc/min is less than the expected infusion pressure 308 corresponding to a commanded flow rate of 20 cc/min, and the expected infusion pressure 312 corresponding to a commanded flow rate of 40 cc/min is less than the expected infusion pressure 310 corresponding to a commanded flow rate of 30 cc/min.

In FIG. 3, the dashed lines 314 represent dynamically variable pressure thresholds defining an acceptable infusion pressure range for each expected infusion pressure. For example, in FIG. 3, at 308 where the commanded flow rate is 20 cc/min with an expected pressure of 70 cm H2O, the dynamically variable pressure threshold may be, for example only, ±5 cm H2O. Accordingly, the selected dynamically variable pressure thresholds are located to represent pressures within the acceptable pressure range of 65 cm H2O to 75 cm H2O. Similarly, at 310 where the commanded flow rate is 30 cc/min and the expected pressure is 65 cm H2O, dynamically variable pressure threshold may be maintained at, for example only, ±6 cm H2O.

Further, at 312 where the commanded flow rate is 40 cc/min and the expected pressure is 60 cm H2O, the dynamically variable pressure threshold may be, for example only, ±7 cm H2O. Accordingly, the dynamically variable pressure thresholds are located to represent pressures within the acceptable pressure range of 53 cm H2O to 67 cm H2O. Although the example range shown includes both an upper and lower threshold, some embodiments determine and apply only the lower threshold.

As is apparent from FIG. 3, each commanded flow setting has an expected infusion pressure associated therewith. Accordingly, in use, as the health care provider progressively increases the commanded flow rate with the foot pedal 108, the expected infusion pressure correspondingly decreases. Just as each commanded flow setting has an expected infusion pressure associated therewith, each expected infusion pressure has a threshold pressure that depends on the expected infusion pressure. Accordingly, the threshold pressure is dynamically variable as it varies for any plurality of expected infusion pressures. This is further described below.

The system disclosed herein differs from prior art systems that have a single static threshold that is the same for all inputs. For example, a prior art system may have a single threshold set at, for example, 53 H2O irrespective of the commanded flow. In a prior art system applied to the graph 300, the pressure range then for a flow command at 308 of 20 cc/min and an expected pressure of 70 cm H2O has deviation of 27 cm H2O (the difference between the expected pressure and the single, static threshold pressure), making the conventional system less responsive to pressures deviations than the system discussed herein.

In the graph 300, the expected infusion pressure corresponds to a commanded flow rate. The relationship between these may be determined based on empirical data obtained over time by testing and recording pressures and input device settings and parameters.

The dotted line 316 in FIG. 3 is an exemplary representation of a detected or measured infusion pressure as detected by the irrigation sensor 204 in FIG. 2 as might occur during a surgical procedure. The controller 103 receives data from the sensor 202 indicative of the measured infusion pressure. This detected infusion pressure is compared to the acceptable thresholds defined relative to the expected infusion pressure. So long as the measured pressure is within the range defined by the threshold pressures, the system operates normally. This is represented in FIG. 3 by the dashed lines 314 at the various stages of expected infusion pressure 306. Again, in embodiments where the threshold level is defined only by a lower threshold, so long as the measured infusion pressure is above the lower threshold, the system operates normally.

However, at 318 in the graph 300, as can be seen, the measured infusion pressure 316 decreases or deviates from the expected infusion level 306 by an amount greater than the threshold 314. Accordingly, it falls below the threshold 314 of acceptable infusion pressure. This may be due to, for example, a hose disconnection, a leak, or other undesirable circumstance.

When the measured infusion pressure passes the threshold, the controller 103 generates a fault signal. This fault signal is the first step in a mitigation process arranged to reduce risk to the patient being treated. For example, in some embodiments, the controller 103 activates a visual alert to notify the health care provider that the measured infusion pressure is outside the acceptable range. These visual alerts may include a message displayed on the panel display 104. This may include displaying a warning message, flashing a symbol, or otherwise generating and displaying a visual alert. Some embodiments may include a visual alert on the hand piece 118 or otherwise disposed about the surgical site, such as a flashing LED or other visual signal. Other embodiments include an audible signal generated to alert the health care provider to the unacceptable infusion pressure. Yet others include a tactile signal, such as a vibration that either generates noise or otherwise alerts the health care provider. Other alerts are contemplated and intended to be within the scope of this disclosure.

In addition to alerting the health care provider, the controller 103 may initiate additional mitigation sequences. For example, the controller 103 may instruct the hand piece 108 to halt ultrasonic needle generation, may decrease or halt the vitrectomy cutter, may slow or stop an aspiration pump if used, or perform other mitigating actions. In some embodiments, the action taken may correspond to the amount of deviation from the threshold. For example, a small deviation from the acceptable operating range across the acceptable pressure threshold may result in only a visual indicator, while a greater deviation from the acceptable pressure threshold may result in the controller shutting down the hand piece. Other mitigating systems may be initiated by the controller 103. Once notified, the health care provider can take to steps to identify the case of the infusion pressure deviation and restore the integrity of the system before continuing with the surgery.

In some embodiments the health care provider modifies default thresholds or ranges for the expected infusion pressures. For example, some embodiments of the system 200 permit a user to adjust the range or distance of the pressure threshold from the expected pressures. Accordingly, prior to conducting a surgery, the surgeon may adjust the thresholds, for example, to be closer to the expected pressures. As such, during the surgical procedure, the pressure tolerances are tighter and the system 200 is more responsive to deviations in measured pressure from the expected pressure than the default settings. Alternatively, the user may adjust the thresholds to be further from the expected pressures. During these surgical procedures, the pressure tolerances are looser, and the system 200 is less responsive to deviations in measured pressure from the expected pressure than the default settings.

For purposes of adjusting the thresholds, the exemplary system provides four customizable operating modes or options. These are identified herein as a) system preset fixed, b) surgeon preset fixed, c) system preset percentage, and d) surgeon preset percentage. Each of these is described below.

The system preset fixed operating mode has prestored pressure thresholds for each expected pressure level. Accordingly, the system preset fixed operating mode may include manufacturing default settings. Further, because the levels are fixed, the thresholds may be the same distance or deviation from the expected pressures for a plurality of different expected pressures. For example, the threshold may be set at a pressure level corresponding to 10 cm H2O below the expected pressure for all expected pressure levels.

The surgeon preset fixed operating mode permits a surgeon to control the threshold pressure's distance or deviation from the expected pressures for a plurality of different expected pressures. This may be done by an adjustment feature, where the surgeon can increase or decrease the threshold from a default setting. For example the surgeon may enter a command to decrease the distance or deviation of the threshold from the expected pressures for example, by adjusting the threshold from a pressure level corresponding to 10 cm H2O, for example, to a pressure level corresponding to 8 cm H2O, for example. It likewise could be increased. Alternatively some embodiments permit the surgeon to enter the desired threshold level directly. For example in these embodiments, the surgeon may enter a value, such as, for example, 8 cm H2O to indicate the distance or deviation of the threshold from the expected pressures. These inputs may be entered through the input device corresponding to the controller, such as for example, the touch display panel, a keyboard, mouse, pointer, voice recognition system, or other input device.

The system preset percentage operating mode has a prestored pressure threshold based on the percentage of the expected pressure level. Accordingly, in this embodiment, the distance or deviation of the threshold from the expected pressures varies depending on the expected pressure. For example, if the expected pressure is 100 cm H2O, the controller may select the distance or deviation of the threshold from the expected pressures to vary by 10%. Thus, the lower threshold pressure is set at 90 cm H2O. However, if the expected pressure is 50 cm H2O, the lower threshold pressure is set at 45 cm H2O, which is 10% of the pressure setting.

The surgeon preset percentage operating mode permits a surgeon to control the threshold pressure's distance or deviation from the expected pressures as a percentage of the expected pressures. Accordingly, as in the surgeon preset fixed operating mode, the surgeon may manually adjust or directly input a deviation percentage. Accordingly, the surgeon may enter a command to decrease the deviation percentage of the threshold as a function of the expected pressures by adjusting the percentage. In this mode, the surgeon can manually increase or decrease, or directly enter, a percentage deviation. For example, the surgeon can adjust the deviation to be 5% of the expected pressure level. Again, these inputs may be entered through the input device corresponding to the controller, such, as for example, the touch display panel, a keyboard, mouse, pointer, voice recognition system, or other input device.

In some embodiments, the controller 103 is configured to take into account variables such as selected tip, infusion sleeve, and others (as these variables can affect the pressure drop). By compensating the expected pressure level for these variables, the controller can predict the expected infusion pressure under normal operating condition for various aspiration flow rates. Due to its dynamic monitoring, the controller can maintain tight threshold limits for relatively precise monitoring for fault conditions.

Figure 4:
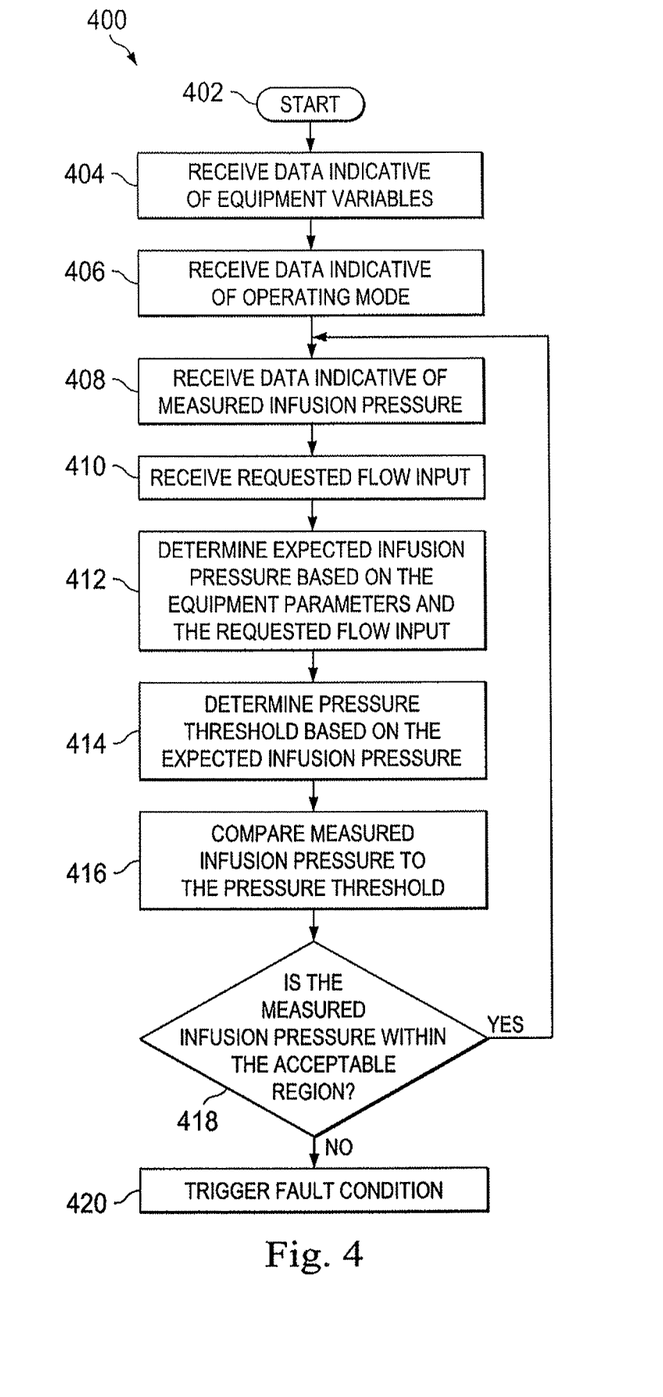
FIG. 4 is a flow diagram illustrating an exemplary method of monitoring the infusion pressure to determine a dynamically variable pressure threshold and to monitor the actual infusion pressure for undesirable pressures.

FIG. 4 shows a flow chart providing an exemplary process 400 executable by the controller 103 for monitoring the infusion pressure during a phacoemulsification or vitrectomy procedure. The process 400 begins at a start and initialization step 402.

At a step 404, the controller 103 optionally receives data indicative of equipment variables. The infusion flow of a system set-up for surgery, for example, having an infusion sleeve and an ultrasound tip or I/A tip, is significantly lower than the available infusion flow through the irrigation luer of a fluid management system or cassette with no attachment, tip and infusion sleeve. In addition, these equipment variables may include system operating parameters, such as the commanded aspiration pump flow, vacuum level, or bottle height. These equipment variables therefore, can affect the infusion pressure drop for a commanded flow rate.

At a step 406, in embodiments having the capability, the controller 103 receives data indicative of the operating mode. This may include the surgeon selecting a mode with an input device. Four example operating modes are discussed above. In some embodiments, the controller may be configured to select a default operating mode in the absence of an input to choose otherwise.

If the controller 103 is operating in a mode allowing user adjustment of the acceptable pressure threshold, then the controller 103 receives and stores the user adjustment. As indicated above, this may be a direct input, a selection of options, an increase, or a decrease of a value representing the acceptable pressure threshold. Also, as explained above, in some embodiments, this may be a desired fixed range, while in other embodiments, this may be percentage of the expected pressure level. The system may be programmed to operate under other arrangements and variances, such as having non-linear or quadratic relationships between the expected pressure and the threshold value. However, for simplicity, only fixed range and percentage range are discussed in detail.

At a step 408, the controller 103 begins receiving data from the sensor 204 indicative of the measured infusion pressure. At a step 410, the controller 103 receives a commanded flow from the flow command input device, which in the embodiment shown, is a foot pedal 108. As described above, in this embodiment, the commanded flow corresponds to the displacement of the foot pedal 108. Accordingly, the commanded flow varies as the foot pedal displacement varies. In response, the controller 103 may operate the fluidics subcomponent of the system 100 in a manner known in the art to provide the commanded fluid flow to surgical site.

At a step 412, the controller 103 determines the expected infusion pressure based on the equipment parameters from step 404 and the real-time commanded flow input from step 410. Since the commanded flow varies based upon user input, this expected infusion pressure also varies.

At a step 414, the controller 103 determines the pressure threshold based on the expected infusion pressure. This takes into account any inputs received from a surgeon at step 406, such as desired pressure or desired range. In addition, because the pressure threshold is based on the expected infusion pressure, the pressure threshold level is different for each change in expected infusion pressure. Likewise, since the expected infusion pressure is dependent on the commanded flow, the pressure threshold is indirectly dependent on the commanded flow. The pressure threshold identifies the limits of an acceptable infusion pressure for the particular expected infusion pressure value. The pressure threshold may be a range, such as plus or minus a particular value or values, or may include only a lower pressure threshold. When only a single threshold, such a lower threshold is identified by the controller, the acceptable pressure range, naturally extends from the lower threshold to an infinite pressure.

At a step 416, the controller 103 compares measured infusion pressure to the pressure threshold and at step 418, queries whether the measured infusion pressure is within the acceptable range of pressures. If yes, then the process returns to step 408 and the controller continues to monitor for any deviation of the measured pressure outside the acceptable pressure range.

If the answer at step 418 is no, then at step 420, the controller 103 triggers a fault condition that initiates a mitigating process. The mitigating process may include alerting the health care provider, or in some instances, halting operation of the hand piece, pump, or other equipment.

In some embodiments, the mitigating steps taken depend on the amount of pressure deviation beyond the pressure threshold. For example, for a small deviation, the controller 103 may only alert the surgeon with a visual, audible, or tactile indicator, while in response to a greater deviation, the controller may halt the equipment.

Therefore, the system described herein recognizes the expected infusion pressure based on normal operating system parameters and/or equipment variables. Thus, when a large aspiration flow is produced, the system recognizes the expected infusion pressure drop and monitors the event on a continuous basis, in a relatively precise manner using a dynamically variable minimum threshold pressure. When the infusion pressure falls below the threshold pressure, or otherwise outside of an acceptable range, the system can respond appropriately.

Although described herein as responsive to a flow command, some embodiments of the system operate using a pressure input command. The system operates similar to that described above, but is control based on a direct pressure input. Accordingly, in response to an input, such as an input from the foot pedal 108, the controller 103 generates a pressure command, and the machine 100 provides irrigation fluid flow through the irrigation line at the commanded pressure. As described above, the commanded pressure may correspond to the displacement of the input device, such as the foot pedal. Other variations are also contemplated.

Accordingly, the system described herein detects undesirable events leading to infusion pressure drop. This may include inadvertent disconnection of the infusion fluid, a kinked irrigation line, depletion of the fluid source, leaking at connectors, or other undesirable events. It then takes appropriate steps to reduce or eliminate any potentially hazardous condition.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of operating a phacoemulsification machine, the method comprising:
   receiving measured pressure data at a controller indicative of a measured infusion pressure;
   receiving from an input device a variable fluid pressure or flow command;
   determining a variable expected fluid pressure value corresponding to the variable fluid pressure or flow command;
   determining whether the measured infusion pressure data is within an acceptable pressure range for the expected fluid pressure value, the acceptable pressure range being defined by a dynamically variable threshold value;
   triggering a fault condition when the measured infusion pressure data is not within the acceptable pressure range; and
   changing an operating parameter of the phacoemulsification machine in response to the fault condition;
   wherein determining a variable expected fluid pressure value corresponding to the variable flow command comprises taking into account data indicative of equipment variables.

2. The method of claim 1, comprising determining the dynamically variable threshold value based on the variable expected fluid pressure value.

3. The method of claim 1, comprising determining the acceptable pressure range based upon a percentage of the expected fluid pressure value for the variable flow command.

4. The method of claim 1, comprising determining the acceptable pressure range based upon a fixed deviation from the expected fluid pressure value for the variable flow command.

5. The method of claim 1, wherein changing an operating parameter of the phacoemulsification machine includes interrupting operation of one of an ultrasound hand piece and an aspiration pump operation.

6. A method of operating a phacoemulsification machine, the method comprising:
   providing an irrigation path configured to carry an irrigation solution to a surgical site;
   providing a fluid sensor configured to detect a fluid parameter in the irrigation path;
   providing an input device configured to receive a command from a health care provider commanding an irrigation fluid pressure or flow through the irrigation path at a pressure or flow rate corresponding to the command;
   receiving equipment data indicative of a tip and infusion sleeve; and
   determining an expected fluid pressure value and a dynamically variable threshold pressure value based upon the command and the equipment data.

7. The method of claim 6, further comprising:
   comparing the detected fluid parameter to the determined dynamically variable threshold pressure value and triggering a fault condition when the detected fluid parameter is less than the determined dynamically variable threshold pressure value.

8. The method of claim 7, further comprising:
   generating a command selected from the list of commands consisting of: display a message, decrease power delivery, and alert the user using at least one of tactile, audible, and visual signals.

9. The method of claim 6, wherein providing an input device further comprises providing a foot pedal operable by the health care provider to generate the variable fluid flow command.

10. The method of claim 6, further comprising:
    providing a second input device configured to receive threshold pressure value calculation data; and
    determining the dynamically variable threshold pressure value based upon the expected pressure value.

11. The method of claim 6, further comprising:
    providing a second input device; and
    receiving data indicative of a selectable operating mode from the second input device.

12. A method of monitoring infusion pressure in a surgical machine, the method comprising:

providing a hand piece having a tip and an infusion sleeve, the hand piece configured to perform a surgical procedure on a patient at a surgical site;

providing an irrigation path associated with the hand piece and configured to carry an irrigation solution to the surgical site;

providing a fluid sensor configured to detect a fluid pressure in the irrigation path;

providing a foot pedal configured to receive a variable fluid command from the health care provider commanding an irrigation fluid characteristic through the irrigation path corresponding to the command;

receiving equipment data indicative of the tip and infusion sleeve;

determining an expected fluid pressure value based upon the variable fluid command and the equipment data; and determining a dynamically variable threshold pressure value based upon the expected fluid pressure value.

13. The method of claim 12 further comprising:

comparing the detected fluid parameter to the determined dynamically variable threshold pressure value and triggering a fault condition when the detected fluid parameter is less than the determined dynamically variable threshold pressure value.

14. The method of claim 13 further comprising:

generating a command selected from the list of commands consisting of: display a message, decrease power delivery, and alert the user using at least one of tactile, audible, and visual signals.

15. The method of claim 12 further comprising:

receiving data indicative of an operating mode from the input device.

16. The method of claim 12 further comprising:

receiving pressure threshold modification data from the input device.

* * * * *